United States Patent [19]

Perregaard et al.

[11] Patent Number: 5,703,087
[45] Date of Patent: Dec. 30, 1997

[54] PHENYL INDOLE COMPOUNDS

[75] Inventors: Jens Kristian Perregaard, Jaegerspris; Ejner Knud Moltzen, Gentofte; Kim Andersen, Rodovre; Henrik Pedersen, Broenshoej; Klaus Peter Bøgesø, Hørsholm, all of Denmark; Andre Pernet, Bannockburn, Ill.; Barbara Bopp, Lake Bluff, Ill.; Darcy Mulford, Lindenhurst, Ill.; Kiyoshi Sakamoto, Sanda, Japan

[73] Assignee: H. Lundbeck A/S, Copenhagen-Valby, Denmark

[21] Appl. No.: 635,905

[22] PCT Filed: Oct. 28, 1994

[86] PCT No.: PCT/DK94/00407

§ 371 Date: Nov. 27, 1996

§ 102(e) Date: Nov. 27, 1996

[87] PCT Pub. No.: WO95/12591

PCT Pub. Date: May 11, 1995

[30] Foreign Application Priority Data

Nov. 1, 1993 [DK] Denmark .................. 1234/93

[51] Int. Cl.$^6$ .................. A61K 31/445; C07D 401/14
[52] U.S. Cl. .................. 514/278; 514/323; 546/15; 546/201
[58] Field of Search .................. 514/323, 278; 546/201, 15

[56] References Cited

U.S. PATENT DOCUMENTS 4,710,500 12/1987 Perregaard .................. 514/254
5,112,838 5/1992 Perregaard et al. .................. 514/323

Primary Examiner—Joseph McKane
Attorney, Agent, or Firm—Darby & Darby

[57] ABSTRACT

The present invention relates to phenylindole compounds of formula I:

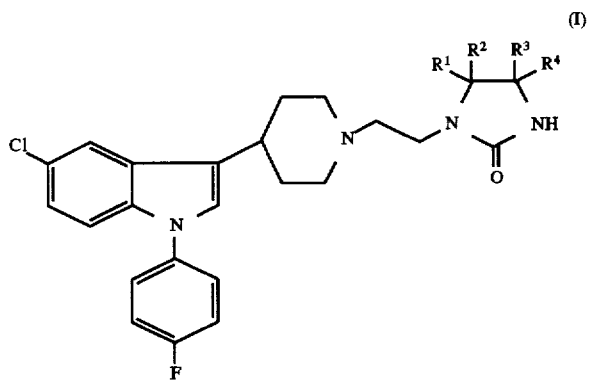

related to atypical neuroleptic sertindole.

6 Claims, No Drawings

PHENYL INDOLE COMPOUNDS

This application is a 371 of PCT/DK94/00407 filed Oct. 28, 1994.

FIELD OF INVENTION

The present invention is concerned with a class of novel phenylindole compounds related to the atypical neuroleptic sertindole (1-[2-[4-[5-chloro-1-(4-fluorophenyl)-1H-indol-3-yl]piperidin-1-yl]ethyl]-2-imidazolidinone), however being substituted in the 4- and/or 5-position of the imidazolidinone ring. Said compounds or a salt or prodrug thereof are useful as antipsychotics, antidepressants, antihypertensives and/or in the treatment of extrapyramidal side effects induced by antipsychotic drugs and negative symptoms of schizophrenia.

BACKGROUND OF THE INVENTION

U.S. Pat. No. 4,710,500 corresponding to EP 200,322 B discloses in general optionally 5-substituted 1-aryl-3-(4-piperidyl)-, 1-aryl-3-(1-piperazinyl)- or 1-aryl-3-(1,2,3,6-tetrahydro-4-pyridyl)indole derivatives having hydrogen or alkyl, alkenyl or certain heterocycle-lower alkyl substituents at the nitrogen atom in the piperidyl, piperazinyl or tetrahydropyridyl group.

Most of the compounds were shown to be potent and long-lasting centrally acting dopamine antagonists in vivo, and accordingly to be useful in the treatment of psychoses, and all the compounds were proven to be strong centrally acting 5-HT$_2$ receptor antagonists in vivo indicating effects in the treatment of depression, extrapyramidal side effects induced by antipsychotic drugs and negative symptoms of schizophrenia. The antipsychotic activity of one compound, i.e. the atypical neuroleptic compound sertindole (recommended INN name), 1-[2-[4-[5-chloro-1-(4-fluorophenyl)-1H-indol-3-yl]piperidin-1-yl]ethyl]-2-imidazolidinone, is described in U.S. Pat. No. 5,112,838 corresponding to EP 392,959A.

In our International Patent Application Publ. No. WO 92/00070 a subclass of the 3-(4-piperidyl) compounds, including sertindole, were found to show anxiolytic activity. Furthermore, said 3-(4-piperidyl) compounds have been reported to be useful in the treatment of hypertension, drug abuse and cognitive disorders (International Patent Publications Nos. WO 92/15301, WO 92/15302 and WO 92/15303).

Metabolism studies have shown that a major circulating metabolite of the antipsychotic compound sertindole exists in humans. It is believed that prevention of the formation of said major metabolite might be advantageous.

Accordingly, the object of the invention is to provide novel drugs having a similar pharmacological profile to that of sertindole, in which drugs, however, the formation of said metabolite is either delayed or prevented.

SUMMARY OF THE INVENTION

It has now been found that said major circulating metabolite of sertindole is the compound 1-[2-[4-[5-chloro-1-(4-fluorophenyl)-1H-indol-3-yl]piperidin-1-yl]ethyl]-1,3-dihydroimidazol-2-one which is structurally identical to sertindole except for the double bond in the 1,3-dihydroimidazol-2-one ring. Furthermore, a class of novel phenylindole compounds related to sertindole, wherein the metabolic transformation of the imidazolidinone ring to a 1,3-dihydroimidazol-2-one ring is delayed or blocked, have been found to show a similar pharmacological profile to that of sertindole.

Accordingly, the present invention relates to novel compounds having general Formula I

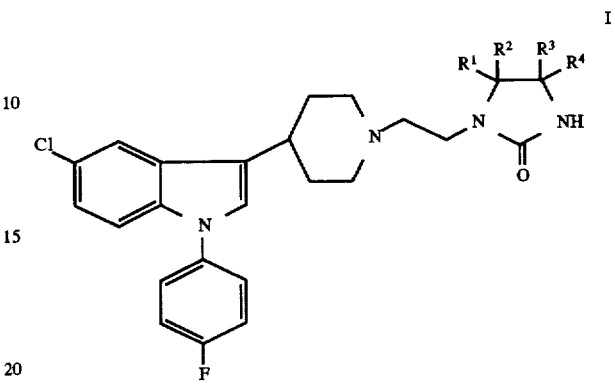

wherein $R^1$-$R^4$ are independently selected from the group consisting of hydrogen, deuterium, halogen, $C_{1-6}$ alkyl, cycloalkyl, cycloalkyl-$C_{1-6}$ alkyl, aryl-$C_{1-6}$ alkyl, aryl, hydroxy, $C_{1-6}$ alkoxy, cycloalkyloxy, cycloalkyl-$C_{1-6}$ alkyloxy, aryl-$C_{1-6}$ alkyloxy, aryloxy, $C_{1-6}$ alkylthio, cycloalkylthio, cycloalky-$C_{1-6}$ alkylthio, aryl-$C_{1-6}$ alkylthio and arylthio, with the proviso that all 4 substituents cannot be hydrogen; or at least one pair of substituents ($R^1$,$R^2$ or $R^3$,$R^4$) constitutes an oxo group or a thioxo group and, if only one oxo or thioxo group is present, the other two substituents are selected from the above group defined for $R^1$-$R^4$, with the proviso that they may not both be hydrogen; or $R^1$ and $R^2$ and/or $R^3$ and $R^4$, respectively, are joined together to form a 3–8 membered spiro ring optionally containing one oxygen or sulfur atom in the ring;

or a prodrug or acid addition salt thereof.

In another aspect the invention relates to a method for the preparation of the novel compounds of Formula I.

In yet another aspect the invention relates to a pharmaceutical composition comprising a novel compound of Formula I together with a suitable pharmaceutically acceptable carrier or diluent.

In yet another aspect the invention relates to the use of the compounds of Formula I for preparing a pharmaceutical composition for treatment of psychosis, depression, negative symptoms of schizophrenia, hypertension or extrapyramidal side effects induced by antipsychotic drugs.

The compounds of the invention have been found to show a pharmacological profile similar to that of sertindole, whereas they are not liable to or less liable to transformation of the imidazolidinone ring into a 1,3-dihydroimidazol-2-one ring, which transformation takes place with respect to sertindole. The pharmacological profile of the compounds of the invention indicates that they are useful in the treatment of the above mentioned disorders.

DETAILED DESCRIPTION OF THE INVENTION

Some of the compounds of general Formula I may exist as optical isomers thereof, and such optical isomers are also embraced by the invention.

In general Formula I halogen means fluoro, chloro, bromo or iodo.

The term cycloalkyl designates a carbocyclic ring having 3–8 carbon atoms, preferably 3–6 carbon atoms, inclusive, or a bicyclic or tricyclic carbonring such as adamantyl.

The terms $C_{1-6}$ alkyl, $C_{1-6}$ alkoxy, $C_{1-6}$ alkylthio, etc. designate such branched or unbranched groups having from one to six carbon atoms inclusive, preferably from one to four carbon atoms. Exemplary of such groups are methyl, ethyl, 1-propyl, 2-propyl, 1-butyl, 2-butyl, 2-methyl-2-propyl, 2-methyl-1-propyl, methoxy, ethoxy, 1-propoxy, methylthio, ethylthio, 1-propylthio, 2-propylthio, methylsulfonyl, ethylsulfonyl, or the like.

The term aryl is intended to mean a carbocyclic or heterocyclic aromatic group optionally comprising one or more substituents independently selected from hydrogen, halogen, lower alkyl, lower alkoxy, hydroxy, lower alkylthio, lower alkyl- or di-alkylamino, cyano, trifluoromethyl, and trifluoromethylthio. Exemplary of such aryl groups are phenyl, thienyl and furanyl.

The pharmaceutically acceptable acid addition salts of the compounds used in the invention are salts formed with non-toxic organic or inorganic acids. Exemplary of such organic salts are those with maleic, fumaric, benzoic, ascorbic, embonic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic and theophylline acetic acids, as well as the 8-halotheophyllines, for example 8-bromo-theophylline. Exemplary of such inorganic salts are those with hydrochloric, hydrobromic, sulfuric, sulfamic, phosphoric and nitric acids.

Prodrugs of the compounds of the invention may be analogous to the prodrugs of sertindole disclosed in our International Patent Application WO 92/06089, or they may be esters of $C_1$-$C_{18}$ carboxylic acids formed with possible hydroxy groups on the imidazolidinone ring.

In a preferred embodiment of the invention $R^1$-$R^4$ are individually selected from the group consisting of hydrogen, deuterium, $C_{1-6}$ alkyl, hydroxy and $C_{1-6}$ alkoxy; or one or both pair of substituents ($R^1$, $R^2$ or $R^3$, $R^4$) constitute an oxo group or $R^1$ and $R^2$ and/or $R^3$ and $R^4$, respectively are linked to form a 3–8 membered spiro ring.

Preferably, both substituents of at least one pair of substituents ($R^1$, $R^2$ or $R^3$, $R^4$) are different from hydrogen or constitute together an oxo group.

According to the invention the novel compounds of formula I, are prepared by a method comprising:

a) reacting the 1-unsubstituted piperidine II with a compound of formula III:

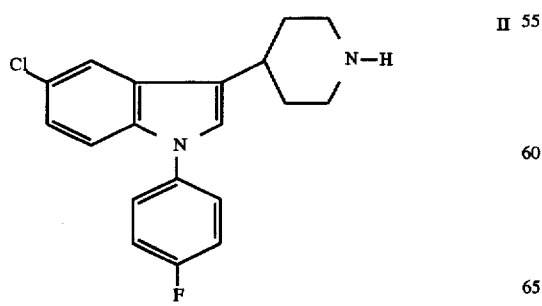

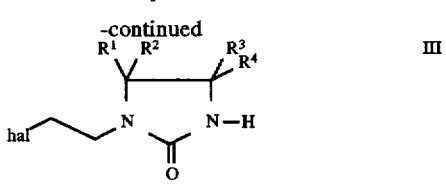

wherein $R^1$-$R^4$ are as previously defined, and "hal" is chloro, bromo, or iodo;

b) reducing an oxo compound of Formula IV or V to a corresponding hydroxy or methylene derivative:

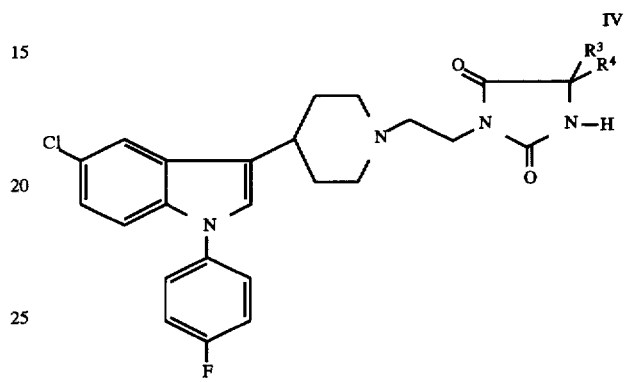

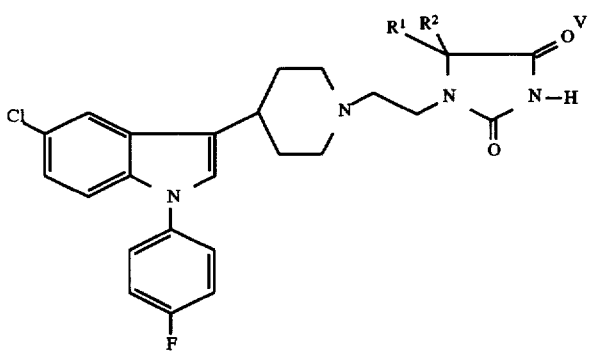

wherein $R^1$-$R^4$ are as previously defined;

c) reacting an urea derivative VI with a bifunctional group, VII, whereby this group is inserted to form the ethylene bridge of compound I:

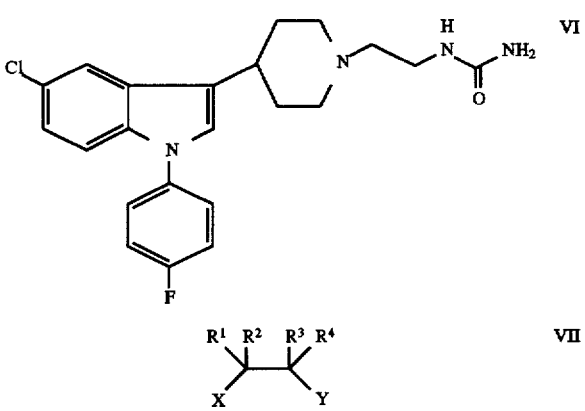

wherein $R^1$-$R^4$ are as previously defined, and X and Y are chlorine, bromine, iodine, $C_{1-6}$ alkoxy or hydroxy;

d) reacting a compound of Formula VIII with an alcohol of Formula $R^{1'}$OH:

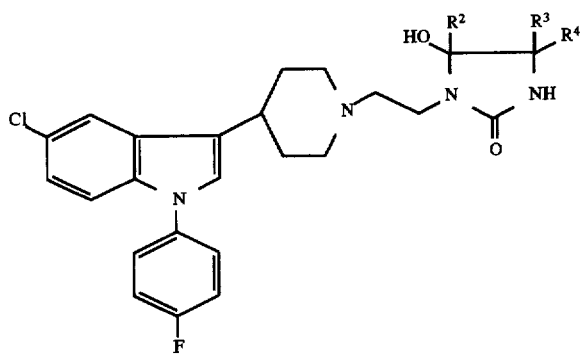

VIII wherein $R^2$-$R^4$ are as previously defined, and $R^{1'}$ is $C_{1-6}$ alkyl, cycloalkyl, cycloalkyl-$C_{1-6}$ alkyl, aryl-$C_{1-6}$ alkyl, or aryl;

e) deprotecting a compound of Formula IX, X or XI:

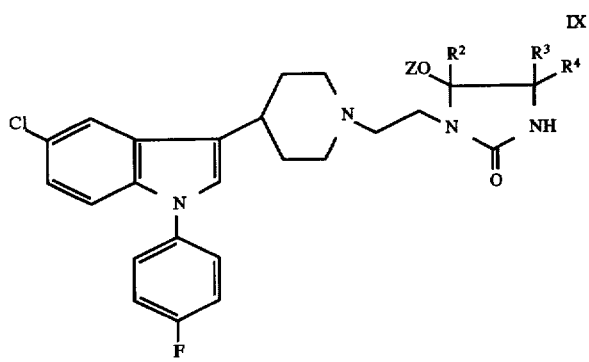

IX

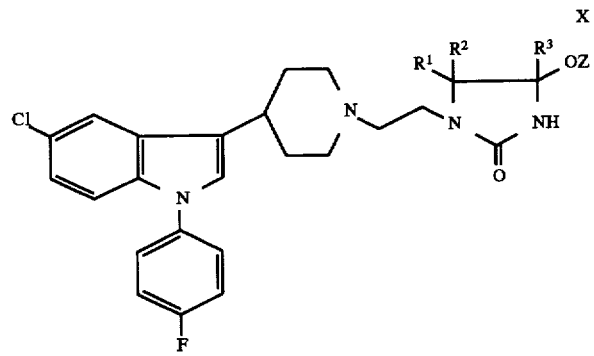

X

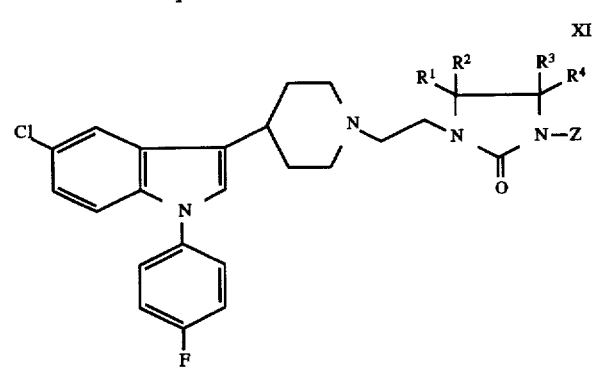

XI wherein $R^1$-$R^4$ are as previously defined, and the protecting group Z is trialkylsilyl, benzyl, acyl, or another protecting group removable under non-acidic conditions; or f) ringclosure reaction of an ethylene diamine derivative of Formula XII:

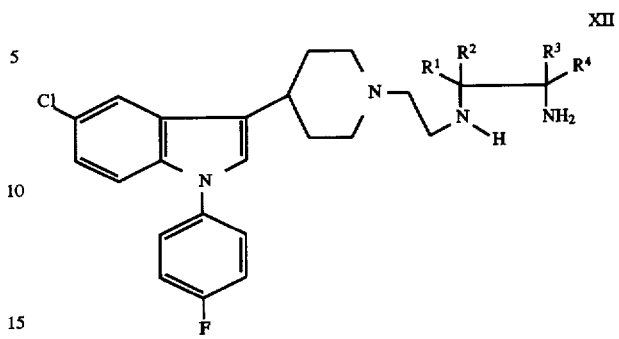

XII wherein $R^1$-$R^4$ are as previously defined, using urea, phosgene, dialkyl carbonate or carbamates to incorporate a carbonyl group to form the heterocyclic ring of Formula I.

Preparation of the intermediate II is reported in Perregaard et al. *J. Med. Chem.*, 1992, 35, 1092–1101, and preparation of the intermediate III appears from the Examples. The alkylation of II with III is generally performed at elevated temperatures in an inert solvent such as acetone, methyl isobutyl ketone or N-methyl-2-pyrrolidone in the presence of a base such as e.g. potassium carbonate.

The oxo compounds IV and V are conveniently reduced to the corresponding hydroxy compounds using LiAlH$_4$, AlH$_3$, B$_2$H$_6$ or a BH$_3$ complex under mild conditions, such as cooling in inert solvents as e.g. diethyl ether or dry tetrahydrofuran. Preparation of the oxo compounds is described in the Examples.

Compounds with bifunctional groups VII are e.g. oxalic acid derivatives such as oxalyl chloride or oxalic acid esters or glyoxylic acid derivatives. The reaction of these derivatives with VI is conveniently performed under acidic or neutral conditions.

The reaction of a compound of Formula VIII with an alcohol $R^{1'}$OH is conveniently performed in an inert solvent, or with the alcohol as solvent at room temperature or at elevated temperature.

Protecting groups Z in Formulas IX-XI are removed by methods such as cleavage of a trialkylsilyl protection group with tetraalkylammonium fluoride in an inert solvent or by mild aqueous hydrolysis. Benzyl groups are removed by catalytic hydrogenation using e.g. Pd as a catalyst. Carboxylic acid esters are hydrolyzed under mild neutral or basic conditions well-known to a chemist skilled in the art. The intermediates of Formulas IX-XI may be obtained by methods conventional in the art.

Compounds of Formula XII are prepared according to the methods described in International Patent Application No. WO 92/15302, Chem. Abstr. 117 (1992) 247029 or as shown in the Experimental Section. The reaction of XII with urea, dialkyl carbonates or carbamates is generally performed at high temperatures (100°–200° C.) either with the neat components or in an inert aprotic solvent such as N,N-dimethylformamide, N-methyl-2-pyrrolidinone or hexamethylphosphoric triamide. Phosgene as the carbonyl precursor is used at low temperatures in inert solvents such as toluene, tetrahydrofuran, diethyl ether optionally in the presence of a base, such as triethylamine or potassium carbonate.

The acid addition salts of the compounds of the invention are easily prepared by methods well known in the art. The base is reacted with either the calculated amount of organic or inorganic acid in an aqueous miscible solvent, such as acetone or ethanol, with isolation of the salt by concentration and cooling, or reacted with an excess of the acid in an aqueous immiscible solvent such as ethyl ether or chloroform, with the desired salt separating directly. These salts may also be prepared by the classical method of double decomposition of appropriate salts.

The compounds of general Formula I, the prodrugs thereof and the pharmaceutically acceptable acid addition salts thereof may be administered in any suitable way, e.g. orally or parenterally, and the compounds may be presented in any suitable form for such administration, e.g. in the form of tablets, capsules, powders, syrups or solutions or dispersions for injection. The prodrugs may conveniently be administered as depot preparations for injection, dissolved in proper oils.

An effective daily dose of the a compound of general Formula I or a pharmaceutically acceptable salt thereof is from 10 µg/kg to 10 mg/kg body weight.

EXAMPLES

In the following the invention is further illustrated by way of examples which may in no way be construed as limiting for the invention.

All melting points were determined on a Büchi SMP-20 apparatus and are uncorrected. $^1$H NMR spectra were recorded at 250 MHz on a Bruker AC 250 spectrometer. Deuterated chloroform (99,8%D) or dimethylsulfoxide (99, 9%D) were used as solvents. TMS was used as internal reference standard. Chemical shift values are expressed in ppm-values. The following abbreviations are used for multiplicity of NMR signals: s=singlet, d=doublet, t=triplet, q=quartet, h=heptet, dd=double doublet, dt=double triplet, dq=double quartet, tt=triplet of triplets, m=multiplet.

Example 1 (method b)

1-[2-[4-[5-chloro-1-(4-fluorophenyl)-1H-indol-3-yl] piperidin-1-yl]ethyl]-5-hydroxyimidazolidin-2-one, 1

1-(2-chloroethyl)imidazolidin-2,5-dione, 1a

To a suspension of glycine (49 g) in water (750 ml) was added sodium hydroxide (39 g) and the mixture was subsequently cooled to 0° C. 2-Chloroethylisocyanate (75 g) was added dropwise at 0°–10° C. during ½ hour. The mixture was stirred for another hour at 10° C. pH was adjusted to 1 by addition of concentrated hydrochloric acid. The precipitated glycine derivative was filtered off, washed with water and finally dried in vacuo. Yield: 106 g, mp: 146°–149° C. All of the glycine derivative thus obtained was suspended in concentrated hydrochloric acid (520 ml) and heated to reflux for 20 minutes. The acidic solvent was evaporated in vacuo. The remaining crude product was dissolved in dichloromethane and dried (anh.MgSO$_4$). Dichloromethane was evaporated, and the crystalline product was recrystallized from ethyl acetate, yielding 62 g of the title compound 1a. Mp: 112°–114° C.

1-[2-[4-[5-chloro-1-(4-fluorophenyl)-1H-indol-3-yl] piperidin-1-yl]ethyl]-5-hydroxyimidazolidin-2-one, 1

A suspension of 5-chloro-1-(4-fluorophenyl)-3-(4-piperidinyl)-1H-indole (45 g) (prepared as described in *J. Med. Chem.* 1992, 35, 1092–1101), 1-(2-chloroethyl) imidazolidin-2,5-dione, 1a (45 g), potassium carbonate (40 g), and potassium iodide (10 g) was refluxed for 5 hours in methyl isobutyl ketone (MIBK) (400 ml). The mixture was filtered while still hot, and MIBK was subsequently evaporated in vacuo. The remaining crude product was purified by column chromatography on silica gel using a mixture of ethyl acetate/ethanol/triethylamine (90:10:4) as eluent. The resulting pure hydantoin derivative was recrystallized from ethyl acetate. Yield: 21 g, mp: 165°–166° C. The thus obtained hydantoin derivative (7 g) was dissolved in dry THF (250 ml). A solution of LiAlH$_4$ (0.7 g) in dry THF (50 ml) was added dropwise at 5°–10° C. The mixture was finally stirred for 5 hours at room temperature. After cooling to 0° C. aqueous NaOH (1.2 ml) and water (3 ml) were cautiously added. Inorganic salts were filtered off, the solvents evaporated in vacuo and the remaining crude solid recrystallized from ethyl acetate. Yield 5.3 g of the title compound 1, mp: 174°–175° C. $^1$H NMR (δ, CDCl$_3$): 8.45 (broad s, 1H), 7.60 (d, 1H), 7.40–7.30 (m, 3H), 7.25–7.10 (m, 3H), 7.05 (s, 1H), 5.25 (broad s, 1H), 5.15 (d, 1H), 3.95 (broad d, 1H), 3.60–3.50 (m, 1H), 3.25 (broad d, 2H), 3.05 (t, 2H), 2.85 (tt, 1H), 2.75 (broad t, 1H), 2.55–2.35 (m, 2H), 2.20–2.05 (m, 3H), 1.90–1.75 (m, 2H).

Example 2 (method e)

1-[2-[4-[5-chloro-1-(4-fluorophenyl)-1H-indol-3-yl] piperidin-1-yl]ethyl]-4-hydroxyimidazolidin-2-one, 2

1-[2-[4-[5-chloro-1-(4-fluorophenyl)-1H-indol-3-yl] piperidin-1-yl]ethyl]-imidazolidin-2,4-dione, 2a Potassium cyanate (30 g) was suspended in dichloromethane (400 ml), and trifluoroacetic acid (50 ml) was added dropwise at 5°–8° C. A solution of 5-chloro-3-[1-(N-cyanomethyl-2-aminoethyl)-4-piperidyl]-1-(4-fluorophenyl)-1H-indole (50 g) (International Patent Application No. WO 92/15302, Chem. Abstr. 117 (1992) 247029) in dichloromethane (200 ml) was added with cooling, and the mixture was stirred overnight at room temperature. The reaction mixture was washed twice with cold dilute sodium hydroxide solution, and the organic phase was dried (anh. MgSO$_4$), and the solvent was evaporated in vacuo yielding 53 g of crude urea derivative, which was refluxed in ethanol (700 ml) and concentrated hydrochloric acid (50 ml) for one hour. After cooling to room temperature the mixture was filtered yielding 33 g of the hydrochloric salt of the title compound 2a. The salt was dissolved in a mixture of methanol (150 ml) and triethylamine (33 ml), and after a few minutes the free base crystallized, yielding 24 g of the title compound 2a. Mp: 208°–210° C.

1-[2-[4-[5-chloro-1-(4-fluorophenyl)-1H-indol-3-yl] piperidin-1-yl]ethyl]-3-[N-(tert-butyldimethylsilyl)] imidazolidin-2,4-dione, 2b A solution of 2a (8.24 g) in dichloromethane (500 ml), tetrahydrofuran (150 ml) and triethylamine (10 ml) was heated to reflux. A solution of tert-butyldimethylsilyl chloride (3.35 g) in dichloromethane (100 ml) was added during 15 minutes. After 2 hours another portion of tert-butyldimethylsilyl chloride (3 g) in dichloromethane (50 ml) and triethylamine (10 ml) was added, and after another 2 hours a similar portion of tert-butyldimethylsilyl chloride was added. The mixture was refluxed overnight and was then evaporated in vacuo. The residue was dissolved in dichloromethane and was washed with water and saturated brine. The organic phase was dried (anh. MgSO$_4$), and was evaporated in vacuo to give 12.6 g of the crude title compound 2b as an oil.

1-[2-[4-[5-chloro-1-(4-fluorophenyl)-1H-indol-3-yl] piperidin-1-yl]ethyl]-4-hydroxy-3-[N-(tert-butyldimethylsilyl)]imidazolidin-2-one, 2c To a solution of 2b (16.2 g) in ether (1 l) was added lithium aluminium hydride (1.62 g) in portions during 40 minutes at room temperature. The mixture was stirred for another 20 minutes. The reaction was quenched with water and concentrated sodium hydroxide and the mixture was filtered and evaporated in vacuo. Purification by column chromatography (silica gel, eluent: triethylamine/ethanol/ethyl acetate 4:4:100) gave 10.1 g of the title compound 2c, Mp: 154°–155° C.

1-[2-[4-[5-chloro-1-(4-fluorophenyl)-1H-indol-3-yl]
piperidin-1-yl]ethyl]-4-hydroxyimidazolidin-2-one, 2

A solution of tetrabutylammonium fluoride, trihydrat (1.5 g) in tetrahydrofuran (600 ml) was cooled to −53° C. A solution of 2c (1.5 g) in tetrahydrofuran (300 ml) was added during 15 minutes at −53° C. The mixture was stirred at −53° C. for another 90 is minutes, and was then cooled to −70° C. and poured on saturated sodium chloride solution at 10° C. The mixture was extracted with dichloromethane, and the organic phase was washed with saturated brine, dried (anh. MgSO$_4$) and evaporated in vacuo at room temperature. The residue was redissolved in ethyl acetate and was shaken with saturated brine, and then concentrated aqueous ammonia was added to pH 12. The organic phase was dried (anh. MgSO$_4$) and evaporated in vacuo at room temperature. Purification by column chromatography (silica gel, eluent: triethylamine/ethanol/ethyl acetate 15:15:70) gave the title compound, which was crystallized from ethyl acetate to yield 0.294 g of 2. Mp.: 176°–178° C.

$^1$H NMR (δ, DMSO-d$_6$) 7.70 (d, 1H), 7.62–7.58 (m, 2H), 7.47 (s, 1H), 7.47–7.34 (m, 3H), 7.16 (dd, 1H), 7.00 (s, 1H), 5.82 (d, 1H), 5.02 (t, 1H), 3.56 (dd, 1H), 3.28–3.17 (m, 2H), 3.13 (dd, 1H) 2.99 (broad d, 2H), 2.80 (tt, 1H), 2.42 (t, 2H), 2.11 (broad t, 2H), 1.95 (broad d, 2H), 1.69 (broad q, 2H).

Example 3 (method d)

1-[2-[4-[5-chloro-1-(4-fluorophenyl)-1H-indol-3-yl]
piperidin-1-yl]ethyl]-5-methoxyimidazolidin-2-one, fumarate 3

A solution of 1-[2-[4-[5-chloro-1-(4-fluorophenyl)-1H-indol-3-yl]piperidin-1-yl]ethyl]-5-hydroxyimidazolidin-2-one (compound 1) (3 g) in methanol (1000 ml) was refluxed for 24 hours. Excess methanol was evaporated in vacuo. The remaining crude product was dissolved in acetone, and fumaric acid (0.75 g) was added. Upon heating the title compound 3 crystallized as the fumarate salt. Yield: 2.7 g, mp: 126°–127° C. $^1$H NMR (δ, DMSO-d$_6$): 7.75 (d, 1H), 7.65–7.55 (m, 2H), 7.50 (s, 1H), 7.50–7.30 (m, 3H), 7.15 (dd, 1H), 6.65 (broad s, 1H), 6.60 (s, 2H), 5.10 (d, 1H), 3.60–3.45 (m, 1H), 3.40–3.15 (m, 5H), 3.15 (s, 3H), 2.95 (broad t, 1H), 2.80 (t, 2H), 2.55 (t, 2H), 2.05 (broad d, 2H), 2.00–1.80 (m, 2H).

Example 4 (method a)

1-[2-[4-[5-Chloro-1-(4-fluorophenyl)-1H-indol-3-yl]
piperidin-1-yl]ethyl]-4,4,5,5-tetradeuteroimidazolidin-2-one, 4.

N-(2-Benzyloxyethyl)oxamide, 4a.

A solution of 2-benzyloxyethylamine (25 g) and potassium carbonate (50 g) in dichloromethane (500 ml) was treated dropwise with methyl chlorooxoacetate (25 g) at 0° C. After stirring for 3 h at room temperature, the mixture was washed with aq. sodium bicarbonate and dried over magnesium sulfate. Removal of solvent in vacuo gave methyl (2-benzyloxyethyl)aminooxoacetate as an oil. Yield: 40 g. The oil was dissolved in tetrahydrofuran, conc. aq. ammonia (500 ml) was added followed by reflux for ½ h. After cooling, the phases were separated, the aqueous phase was extracted with dichloromethane, and the combined organic phases were dried over magnesium sulfate. Removal of the solvent gave 4a as a crystalline material. Yield: 32 g.

2-(2-Benzyloxyethylamino)-1,1,2,2-tetradeuteroethylamine, 4b

A suspension of lithium aluminium deuteride (20 g) in tetrahydrofuran (600 ml) was treated portionwise with 4a (22 g). After reflux for 16 h the mixture was cooled and treated subsequently with water (40 ml), 15% sodium hydroxide (20 ml), and water (100 ml). The mixture was filtered and the precipitate extracted with dichloromethane (1000 ml). The filtrate was concentrated in vacuo and the remaining oil mixed with the dichloromethane phase. Drying over magnesium sulfate and removal of solvent in vacuo gave 4b as a yellow oil. Yield: 19 g.

1-(2-Chloroethyl)-4,4,5,5-tetradeuteroimidazolidin-2-one, 4c.

A mixture of 4b (19 g) and urea (7.5 g) was heated to 180° C. for 1 h. Purification by column chromatography (silica gel, eluent:methanol/ethyl acetate 1:4) gave 1-(2-benzyloxyethyl)-4,4,5,5-tetradeuteroimidazolidin-2-one as an oil. Yield: 13.2 g.

The oil was dissolved in ethanol (200 ml) and 5% Pd/C (3.5 g) was added. The mixture was treated with 4 atm. of hydrogen gas for 16 h. Filtration and removal of solvent gave 1-(2-hydroxyethyl)-4,4,5,5-tetradeuteroimidazolidin-2-one as an oil. Yield: 7.8 g.

The oil was suspended in dry toluene (50 ml). Thionyl chloride (7 ml) and dimethyl formamide (0.5 ml) was added followed by heating to 70° C. for 2 h. The mixture was concentrated in vacuo, brine was added followed by extraction with dichloromethane. Drying over magnesium sulfate and treatment with charcoal gave, after removal of solvent in vacuo, the title compound as a crystalline solid. Yield: 7.4 g.

1-[2-[4-[5-Chloro-1-(4-fluorophenyl)-1H-indol-3-yl]
piperidin-1-yl]ethyl]-4,4,5,5-tetradeuteroimidazolidin-2-one, 4

A mixture of 5-chloro-1-(4-fluorophenyl)-3-(4-piperidinyl)-1H-indole (12.5 g), 4c (4.5 g), potassium carbonate (10 g), and potassium iodide (1 g) in isopropyl methyl ketone was kept at 95° C. for 16 h. The mixture was cooled, filtered, and concentrated in vacuo. Purification by column chromatography (silica gel, eluent:triethylamine/methanol/ethyl acetate 1:2:17) gave the title compound as a solid. Recrystallization from ethanol yielded 7.8 g of crystalline 4. Mp.: 159°–62° C.

$^1$H NMR (δ, CDCl$_3$): 7.64 (d, 1H), 7.45–7.28 (m, 3H), 7.24–7.09 (m, 3H), 7.08 (s, 1H), 5.13 (s, 1H), 3.38 (t, 2H), 3.12–3.01 (m, 2H), 2.89–2.72 (m, 1H), 2.57 (t, 2H), 2.28–2.13 (m, 2H), 2.11–1.98 (m, 2H), 1.90–1.69 (m, 2H).

Example 5 (method a)

1-[2-[4-[5-Chloro-1-(4-fluorophenyl)-1H-indol-3-yl]
piperidin-1-yl]ethyl]-4,4-dideuteroimidazolidin-2-one, 5.

(2-Benzyloxyethyl)aminoacetonitrile, 5a

A mixture of 2-benzyloxyethylamine (40 g) and triethylamine (50 ml) in tetrahydrofuran (500 ml) was treated dropwise with chloroacetonitrile (23 g) at room temperature.

After reflux for 2 h the mixture was cooled and filtered, water (400 ml) was added and the mixture was extracted with dichloromethane. The solvent was removed in vacuo, ether (400 ml) was added and the ether solution was treated with magnesium sulfate and charcoal. Filtration and removal of solvent in vacuo gave 5a as a yellow oil. Yield: 39 g.

2-(2-Benzyloxyethylamino)-1,1-dideuteroethylamine, 5b

A suspension of lithium aluminium deuteride (15 g) in dry tetrahydrofuran (400 ml) was treated portionwise under nitrogen gas with aluminium chloride (23 g) at room temperature. After stirring for ½ h, a solution of 5a (29 g) in tetrahydrofuran (50 ml) was added dropwise followed by reflux for 1 h. After cooling 15% sodium hydroxide (80 ml) was slowly added followed by addition of water (40 ml). The mixture was filtered and the precipitate extracted with dichloromethane (800 ml). The filtrate from the filtration was concentrated in vacuo and the remaining oil mixed with the dichloromethane phase. Drying over magnesium sulfate and removal of solvent in vacuo gave a mixture of 5b and 2-benzyloxyethylmethylamine, 22 g. The mixture was used directly in the next step.

1-(2-Chloroethyl)-4,4-dideuteroimidazolidin-2-one, 5c

The mixture of 5b and 2-benzyloxyethylmethylamine (22 g) and urea (7.5 g) was heated to 180° C. for 1 h. Purification by column chromatography (silica gel, eluent:triethylamine/methanol/ethyl acetate 5:2:93) gave 1-(2-benzyloxyethyl)-4,4-dideuteroimidazolidin-2-one as an oil. Yield: 6.4 g. The oil was dissolved in ethanol (100 ml) and 5% Pd/C (1.5 g) was added. The mixture was treated with 4 atm. of hydrogen gas for 16 h. Filtration and removal of solvent gave 1-(2-hydroxyethyl)-4,4-dideuteroimidazolidin-2-one as an oil. Yield: 3.8 g. The oil was suspended in dry toluene (25 ml). Thionyl chloride (3.5 ml) and dimethyl formamide (0.1 ml) was added followed by heating to 70° C. for 2 h. The mixture was concentrated in vacuo, brine was added followed by extraction with dichloromethane. Drying over magnesium sulfate, treatment with charcoal and removal of solvent in vacuo, gave the title compound as a crystalline solid. Yield: 4.1 g.

1-[2-[4-[5-Chloro-1-(4-fluorophenyl)-1H-indol-3-yl]piperidin-1-yl]ethyl]-4,4-dideuteroimidazolidin-2-one, 5

This compound was prepared by a procedure analogous to the procedure described for the synthesis of 4 using 5c as starting material. Mp.: 159°–62° C.

$^1$H NMR ($\delta$, CDCl$_3$): 7.64 (d, 1H), 7.45–7.28 (m, 3H), 7.24–7.09 (m, 3H), 7.08 (s, 1H), 4.45 (s, 1H), 3.56 (s, 2H), 3.38 (t, 2H), 3.12–3.01 (m, 2H), 2.89–2.72 (m, 1H), 2.57 (t, 2H), 2.28–2.13 (m, 2H), 2.11–1.98 (m, 2H), 1.90–1.69 (m, 2H).

Example 6 (method a)

1-[2-[4-[5-Chloro-1-(4-fluorophenyl)-1H-indol-3-yl]piperidin-1-yl]ethyl]-5,5-dideuteroimidazolidin-2-one, 6

Azido-N-(2-benzyloxyethyl)acetamide, 6a

A solution of 2-benzyloxyethylamine (15 g) and potassium carbonate (40 g) in acetone (400 ml) was treated dropwise with azidoacetyl chloride at 20° C. After stirring for 3 h at room temperature, the mixture was filtered and concentrated in vacuo. Dichloromethane (800 ml) was added, and the solution was washed with aq. sodium bicarbonate. The organic phase was dried over magnesium sulfate. Removal of solvent in vacuo gave a yellow oil which was filtered through silica gel with ethyl acetate. Removal of the solvent in vacuo gave 6a as a colorless oil. Yield: 22 g.

2-(2-Benzyloxyethylamino)-2,2-dideuteroethylamine, 6b

A suspension of lithium aluminium deuteride (10 g) in tetrahydrofuran (300 ml) was treated dropwise with a solution of 6a (14 g) in tetrahydrofuran (50 ml). After reflux for 16 h, the mixture was cooled and subsequently treated with water (20 ml), 15% sodium hydroxide (10 ml), and water (50 ml). The mixture was filtered and the precipitate extracted with dichloromethane (600 ml). The filtrate was concentrated in vacuo and the remaining oil mixed with the dichloromethane phase. Drying over MgSO$_4$ and removal of solvent in vacuo gave 6b as a yellow oil. Yield: 9.4 g.

1-(2-Chloroethyl)-5,5-dideuteroimidazolidin-2-one, 6c

This compound was prepared by a procedure analogous to the procedure described for the synthesis of 4c using 6b as starting material.

1-[2-[4-[5-Chloro-1-(4-fluorophenyl)-1H-indol-3-yl]piperidin-1-yl]ethyl]-5,5-dideuteroimidazolidin-2-one, 6

This compound was prepared by a procedure analogous to the procedure described for the synthesis of 4 using 6c as starting material. Mp.: 160°–62° C. 1H NMR ($\delta$, CDCl$_3$): 7.64 (d, 1H), 7.45–7.28 (m, 3H), 7.24–7.09 (m, 3H), 7.08 (s, 1H), 4.78 (s, 1H), 3.41 (s, 2H), 3.38 (t, 2H), 3.12–3.01 (m, 2H), 2.89–2.72 (m, 1H), 2.57 (t, 2H), 2.28–2.13 (m, 2H), 2.11–1.98 (m, 2H), 1.90–1.69 (m, 2H).

Example 7 (method c)

1-[2-[4-[5-Chloro-1-(4-fluorophenyl)-1H-indol-3-yl]piperidin-1-yl]ethyl]-4-hydroxyimidazolidin-2,5-dione, 7a and 1-[2-[4-[5-chloro-1-(4-fluorophenyl)-1H-indol-3-yl]piperidin-1-yl]ethyl]-5-hydroxyimidazolidin-2,4-dione, 7b 5-Chloro-1-(4-fluorophenyl)-3-[1-(2-ureidoethyl)piperidin-4-yl]-1H-indol, 7c Potassium cyanate (4.9 g) was suspended in dichloromethane (50 ml) followed by dropwise addition of trifluoroacetic acid (4.4 ml) at 0° C. A solution of 3-[1-(2-aminoethyl)piperidin-4-yl]-5-chloro-1-(4-fluorophenyl)-1H-indol (10.8 g) (Pat. Appl. No. WO 9215302, Chem. Abstr. 117 (1992) 247029) in dichloromethane (100 ml) was added dropwise followed by stirring for 6 h at room temperature. Water (100 ml) was added and the reaction mixture made alkaline with conc. ammonia. The phases were separated followed by extraction with dichloromethane. The combined organic phases were dried over magnesium sulfate. Removal of solvent in vacuo gave a heavy oil which was purified by flash chromatography (silica gel, eluent: triethylamine/methanol/ethyl acetate 5:20:75). The title compound was isolated as a crystalline material, mp. 161°–63° C. Yield: 7.9 g.

1-[2-[4-[5-Chloro-1-(4-fluorophenyl)-1H-indol-3-yl]piperidin-1-yl]ethyl]-4-hydroxyimidazolidin-2,5-dione, 7a, and 1-[2-[4-[5-chloro-1-(4-fluorophenyl)-1H-indol-3-yl]piperidin-1-yl]ethyl]-5-hydroxyimidazolidin-2,4-dione, 7b A mixture of 7c (1.6 g) and glyoxylic acid monohydrate (0.5 g) in 80% acetic acid (25 ml) was refluxed for 1 h. The reaction mixture was concentrated in vacuo followed by addition of saturated aq. sodium bicarbonate solution (100 ml). Extraction with dichloromethane, drying of the organic phase over magnesium sulfate and removal of solvent in vacuo gave a heavy oil which was separated by flash chromatography (silica gel, triethylamine/methanol/ethyl acetate 5:2:93).

Fraction 1: crystalline 7a, mp. 128°–35° C. Yield: 0.2 g.

$^1$H NMR ($\delta$, CDCl$_3$): 7.59 (d, 1H), 7.45–7.28 (m, 3H), 7.24–7.08 (m, 4H), 5.35 (s, 1H), 3.71–3.56 (m, 2H), 3.40–3.22 (m, 2H), 3.00–2.54 (m, 3H), 2.32–1.71 (m, 6H).

Fraction 2: crystalline 7b, mp 172°–80° C. Yield: 0.35 g. $^1$H NMR ($\delta$, CDCl$_3$): 7.59 (d, 1H), 7.48–7.29 (m, 3H), 7.28–7.12 (m, 3H), 7.09 (s, 1H), 5.09 (s, 1H), 4.20–4.06 (m, 1H), 3.37–3.01 (m, 3H), 3.00–2.82 (m, 1H), 2.81–2.63 (m, 1H), 2.61–2.42 (m, 2H), 2.32–2.04 (m, 3H), 1.98–1.74 (m, 2H).

Example 8 (method a)

1-[2-[4-[5-Chloro-1-(4-fluorophenyl)-1H-indol-3-yl]piperidin-1-yl]ethyl]-4,4-dimethylimidazolidin-2-one, 8

2-(2-Benzyloxyethylamino)-1,1-dimethylethylamine, 8a

To a mixture of 2-bromo-2-methylpropionylbromid (76 g), K$_2$CO$_3$ (55 g) and dichloromethane (700 ml) was added a solution of 2-benzyloxyethylamine (50 g) in dichloromethane (500 ml) at −10° C. After stirring at room temperature for 1.5 h the mixture was washed with water (500 ml) and dried (MgSO$_4$). Evaporation of the solvents in vacuo afforded N-(2-benzyloxyethyl)-2-bromo-2-methylpropionamide as an oil: 104 g A mixture of the crude amide (104 g), sodium azide (23.6 g) and N-methyl-2-pyrrolidone (500 ml) was heated at 50° C. for 22 h. After cooling to room temperatur water was added and the resulting mixture was extracted with diethyl ether (2×400 ml). The combined organic phases were washed with brine (3×500 ml) and dried (Na$_2$SO$_4$). Evaporation of the solvents in vacuo gave 2-azido-N-(2-benzyloxyethyl)-2-methylpropionamide as an oil:78 g.

A solution of 2-azido-N-(2-Benzyloxyethyl)-2-methylpropionamide (70 g) in THF (750 ml) was added to a suspension of LiAlH$_4$ (20 g) in THF (500 ml) at 0° C. during 1 h. After reflux for 4 h, the mixture was cooled to 0°

C., water (20 ml) and aqueous NaOH (20 ml) were added, the inorganic salts were filtered off and the solvents were dried. Evaporation of the solvents in vacuo gave 8a as an oil: 53 g.

1-(2-Chloroethyl)-4,4-dimethylimidazolidin-2-one, 8b

This compound was prepared by a procedure analogous to the procedure described for the synthesis of 4c using 8a as starting material.

1-[2-[4-[5-Chloro-1-(4-fluorophenyl)-1H-indol-3-yl] piperidin-1-yl]ethyl]-4,4-dimethylimidazolidin-2-one, 8

This compound was prepared by a procedure analogous to the procedure described for the synthesis of 4 using 8b as starting material: mp 142°–144° C.;

$^1$H NMR (CDCl$_3$) δ 7.65 (d, 1H), 7.45–7.30 (m, 3H), 7.25–7.10 (m, 3H), 7.05 (s, 1H), 4.40 (s, 1H), 3.35 (t, 2H), 3.25 (s, 2H), 3.15–3.00 (m, 2H), 2.90–2.70 (m, 1H), 2.60 (t, 2H), 2.30–2.15 (m, 2H), 2.15–2.00, 1.90–1.70 (m, 2H), 1.30 (s, 6H).

Example 9 (method a)

1-[2-[4-[5-Chloro-1-(4-fluorophenyl)-1H-indol-3-yl] piperidin-1-yl]ethyl]-5,5-dimethylimidazolidin-2-one, 9

1-(2-Benzyloxyethyl)-5,5-dimethylimidazolidin-2,4-dione, 9a

A mixture of 2-benzyloxyethylamine (50 g), ethyl 2-bromo-2-methylpropionate (97.5 g) and N-methyl-2-pyrrolidone (1 l) was heated at 100° C. for 7 h. The mixture was cooled to room temperature, water was added and the resulting mixture was extracted with ethyl acetate (2×500 ml). The combined organic phases were washed with water (4×500 ml) and brine (2×500 ml), dried (Na$_2$SO$_4$) and the solvents were evaporated in vacuo. Purification of the remaining oil by column chromatography on silica gel (ethyl acetat containing 4% triethylamine) gave ethyl 2-(2-benzyloxyethylamino)-2-methylpropionate as an oil: 30 g A mixture of ethyl 2-(2-benzyloxyethylamino)-2-methylpropionate (29 g) and urea (8.5 g) was heated at 180° C. for 1 h. After cooling to room temperature water (250 ml) was added and the resulting mixture was extracted with diethyl ether (500 ml). The organic phase was washed with brine (400 ml) and dried (Na$_2$SO$_4$). Evaporation of the solvents in vacuo afforded 9a as an oil: 28 g.

1-(2-Benzyloxyethyl)-5,5-dimethylimidazolidin-2-one, 9b

A solution of 9a (28 g) in THF (250 ml) was added to a suspension of LiAlH$_4$ (8 g) in THF (250 ml) at 20°–25° C. After stirring at room temperature for 1 h, the mixture was cooled to 0° C., water (10 ml) and aqueous NaOH (10 ml) were added, the inorganic salts were filtered and the solvents were evaporated in vacuo. The remaining oil was purified by column chromatography on silica gel (ethyl acetate) yielding 9b as an oil: 10 g.

1-(2-Chloroethyl)-5,5-dimethylimidazolidin-2-one, 9c 9b (9 g) was dissolved in ethanol (150 ml) and 5% Pd/C (2.0 g) was added. The mixture was treated with 3 atm. of H$_2$ gas for 36 h. Filtration and removal of solvent gave 1-(2-hydoxyethyl)-5,5-dimethylimidazolidin-2-one as an oil. Yield: 5.1 g.

The oil was suspended in dry toluene (50 ml). Thionyl chloride (5 ml) and dimethyl formamide (0.5 ml) were added followed by heating to 70° C. for 2 h. The mixture was concentrated in vacuo, brine (100 ml) was added followed by extraction with dichloromethane (100 ml). The organic phase was dried (MgSO$_4$) and the solvents evaporated in vacuo affording the title compound as an oil. Yield: 5 g.

1-[2-[4-[5-Chloro-1-(4-fluorophenyl)-1H-indol-3-yl] piperidin-1-yl]ethyl]-5,5-dimethyloimidazolidin-2-one, 9

This compound was prepared by a procedure analogous to the procedure described for the synthesis of 4 using 9c as starting material. mp 146°–148° C.;

$^1$H NMR (CDCl$_3$) δ 7.65 (d, 1H), 7.45–7.30 (m, 3H), 7.25–7.10 (m, 3H), 7.05 (s, 1H), 4.70 (s, 1H), 3.25 (t, 2H), 3.15 (s, 2H), 3.20–3.05 (m, 2H), 2.90–2.70 (m, 1H), 2.60 (t, 2H), 2.35–2.20 (m, 2H), 2.15–2.00 (m, 2H), 1.95–1.70 (m, 2H), 1.30 (s, 6H).

Example 10 (method f)

1-[2-[4-[5-Chloro-1-(4-fluorophenyl)-1H-indol-3-yl] piperidin-1-yl]ethyl]-5,5-dimethylimidazolidin-2,4-dione, 10

This compound was prepared by a procedure analogous to the procedure described for the synthesis of 9a using 2-[4-[5-chloro-1-(4-fluorophenyl)-1H-indol-3-yl]piperidin-1-yl] ethylamine (prepared as described for similar compounds in J. Med. Chem. 1992, 35, 4813–4822) as starting material. The compound was precipitated as its triethylammonium salt from ethyl acetate. mp 140°–142° C. $^1$H NMR (CDCl$_3$) δ 7.65 (d, 1H), 7.45–7.30 (m, 3H), 7.25–7.10 (m, 3H), 7.05 (s, 1H), 3.65 (q, 6H), 3.45 (t, 2H), 3.20–3.05 (m, 2H), 2.90–2.80 (m, 1H), 2.70 (t, 2H), 2.40–2.20 (m, 2H), 2.15–2.00 (m, 2H), 1.95–1.70 (m, 2H), 1.50 (t, 9 H), 1.45 (s, 6H).

Example 11 (method b)

1-[2-[4-[5-chloro-1-(4-fluorophenyl)-1H-indol-3-yl] piperidin-1-yl]ethyl]-4,5-dihydroxyimidazolidin-2-one, 11

A solution of 7a (0.5 g) in tetrahydrofuran (25 ml) was cooled to 0° C. and treated portionwise with LiAlH$_4$ (15 mg) while strictly keeping the temperature at 0° C. After stirring for 2 h at 0° C. additional LiAlH$_4$ (15 mg) was added portionwise followed by stirring for 2 h at 0° C. The reaction was quenched with water/aq. 4N NaOH followed by removal of solvent in vacuo. Methylene choride (25 ml) was added and the resulting solution dried over MgSO$_4$ and concentrated in vacuo. The remaining oil was purified by flash chromatography (silica gel, eluent:ethyl acetate/methanol/triethylamine 85:10:5). The title compound was obtained as a crystalline material, mp. 190°–92° C. Yield: 74 mg. $^1$H NMR (DMSO-d$_6$) δ 7.70 (d, 1H), 7.65–7.50 (m, 2H), 7.50–7.30 (m, 4H), 7.15 (t, 1H), 4.65 (s, 1H), 4.60 (s, 1H), 3.55–3.05 (m, 3H), 3.00–2.70 (m, 2H), 2.60–2.20 (m, 3H), 2.20–1.85 (m, 3H), 1.85–1.60 (m, 2H).

Example 12

3-[2-[4-[5-Chloro-1-(4-fluorophenyl)-1H-indol-3-yl] piperidin-1-yl]ethyl]-1,3-diazaspiro[4.4]nonan-2-one, 12

1-Azido-N-(2-benzyloxyethyl)cyclopentan-1-carboxamide, 12a

1-Azidocyclopentan-1-carbonylchloride (16.8 g) was added to a mixture of 2-benzyloxyethylamine (14.7 g), K$_2$CO$_3$ (16.6 g) and acetone at 0° C. After stirring at room temperature for 2 h the mixture was filtered, concentrated in vacuo and after addition water (100 ml) extracted with diethyl ether (2×100 ml).The combined organic phases were washed with brine and dried (Na$_2$SO$_4$). Evaporation of the solvents gave the crude 12a as an oil: 22.3 g.

1-(2-benzyloxyethylaminomethyl)cyclopentylamine, 12b

A solution of the crude 1-azido-N-(2-benzyloxyethyl) cyclopentan-1-carboxamide 12a (22.3 g) in tetrahydrofuran (100 ml) was added to a suspension of LiAlH$_4$ (6 g) in tetrahydrofuran (100 ml). After reflux for 2 h the mixture was cooled to 0° C. and subsequently treated with water (6 ml), 15% aqueous NaOH (6 ml) and water (6 ml). The mixture was filtered and the precipitate extracted with dichloromethane (200 ml). Drying of the combined organic phases (MgSO$_4$) and evaporation of the solvents in vacuo afforded the title compound as an oil: 18.7 g.

3-(2-chloroethyl)-1,3-diazaspiro[4.4]nonan-2-one, 12c

This compound was prepared by a procedure analogous to the procedure described for the synthesis of 4c using 12b as starting material.

3-[2-[4-[5-Chloro-1-(4-fluorophenyl)-1H-indol-3-yl]piperidin-1-yl]ethyl]-1,3-diazaspiro[4.4]nonan-2-one, 12d This compound was prepared by a procedure analogous to the procedure described for the synthesis of 4 using 12c as starting material: mp 176°–178° C.;

$^1$H NMR (CDCl$_3$) δ 7.65 (d, 1H), 7.45–7.30 (m, 3 H), 7.25–7.10 (m, 3 H), 7.05 (s, 1 H), 4.75 (s, 1 H), 3.40–3.30 (m, 4 H), 3.15–3.00 (m, 2 H), 2.90–2.70 (m, 1H), 2.55 (t, 2H), 2.30–2.15 (m, 2 H), 2.15–1.95 (m, 2 H), 1.90–1.55 (m, 10 H).

Example 13
1-[2-[4-[5-Chloro-1-(4-fluorophenyl)-1H-indol-3-yl]piperidin-1-yl]ethyl]-1,3-diazaspiro[4.4]nonan-2-one, 13
1-(2-Benzyloxyacetamido)-cyclopentyl-1-carboxamide, 13a Benzyloxyacetylchloride (16.7 g) was added to a mixture of 1-aminocyclopentan-1-carboxamide (10.2 g), K$_2$CO$_3$ (13.3 g) and acetone (150 ml) at −5° to 0° C. After stirring at room temperature for 2 h the reaction mixture was filtered. The precipitate was extracted with diethyl ether (50 ml) washed with water (100 ml) and dried at 50 ° C. in vacuo for 18 h giving the title compound as a crystalline material: 13.8 g.

N-(1-aminomethylcyclopentyl)-N-(2-Benzyloxyethyl) amine, 13b

This compound was prepared by a procedure analogous to the procedure described for the synthesis of 12b using 13a as starting material.

1-(2-Chloroethyl)-1,3-diazaspiro[4.4]nonan-2-one, 13c

This compound was prepared by a procedure analogous to the procedure described for the synthesis of 4c using 13b as starting material.

1-[2-[4-[5-Chloro-1-(4-fluorophenyl)-1H-indol-3-yl]piperidin-1-yl]ethyl]-1,3-diazaspiro-[4.4]nonan-2-one, 13

This compound was prepared by a procedure analogous to the procedure described for the synthesis of 4 using 13c as starting material: mp 143°–145° C.;

$^1$H NMR (CDCl$_3$) δ 7.65 (d, 1 H), 7.45–7.30 (m, 3 H), 7.25–7.10 (m, 3 H), 7.05 (s, 1 H), 4.65 (s, 1 H), 3.30–3.15 (m, 4 H), 3.15–3.05 (m, 2 H), 2.90–2.75 (m, 1 H), 2.60 (t, 2 H), 2.35–2.20 (m, 2 H), 2.10–2.00 (m, 2 H), 1.95–1.50 (m, 10 H).

Pharmacology

The compounds used in the invention were tested in accordance with the following well recognized and reliable test methods.

Inhibition of $^3$H-Ketanserin Binding To 5-HT$_2$ Receptors in Flat Cortex in vitro By this method the inhibition by drugs of the binding of $^3$H-Ketanserin (0.5 nM) to 5-HT$_2$ receptors in membranes from rat is determined in vitro. The method is described in Hyttel, *Pharmacology & Toxicology* 61, 126–129, 1987. The results are shown in Table 1.

Inhibition of $^3$H-Spiperone Binding to Dopamine D$_2$ Receptors in Rat Corpus Striatum in vitro By this method the inhibition by drugs of the binding of $^3$H-spiperone (0.5 nM) to dopamine D$_2$ receptors in membranes from rat corpus striatum is determined in vitro. The method and results for standard compounds are described in Hyttel & Larsen, *J. Neurochem*, 44, 1615–1622, 1985). The results are shown in Table 1.

Quipazine Inhibition

Quipazine is a 5-HT$_2$ agonist, which induces head twitches in rats. The test is an in vivo test for 5-HT$_2$-antagonistic effect measuring the ability to inhibit quipazine induced head twitches. The method and test results for some reference substances are published by Arnt et al. (*Drug Development Research*, 16, 59–70, 1989, attached). The results are shown in Table 2.

Catalepsy

Evaluation of catalepsy is made according to Arnt (Eur. J. Pharmacol. 90, 47–55 (1983)). Test compound is given s.c. in different doses. The rat (170–240 g) is placed on a vertical wire mesh (mesh diameter 12 mm). The rat is considered cataleptogenic if it remains immobile for more than 15 sec. The maximum number of rats showing catalepsy within the first 6 hours is recorded for each dose group. The results are recorded in fractions and an ED$_{50}$ value is calculated by means of log-probit analysis. The results are shown in Table 2.

TABLE 1

RECEPTOR BINDING DATA (IC$_{50}$ values in nM)

| Compound No. | 5-HT$_2$ binding [$^3$H]-ketanserin | Dopamine D$_2$ binding [$^3$H]-spiroperidol |
|---|---|---|
| 1 | 1.4 | 5.5 |
| 3 | 1.5 | 13 |
| 4 | 1.1 | 8.3 |
| 5 | 0.69 | 5.9 |
| 6 | 0.98 | 7.6 |
| 7a | 6.6 | 18 |
| 7b | 9.8 | 23 |
| 8 | 2.0 | 18 |
| 9 | 1.7 | 14 |
| 10 | 12 | 20 |
| 11 | 2.5 | 18 |
| 12 | 4.7 | 19 |
| 13 | 4.5 | 30 |
| sertindole | 0.39 | 4.1 |

TABLE 2

IN VIVO ACTIVITY (ED$_{50}$ values in μmol/kg)

| Compound No | Quipazine inhibition | | Catalepsy |
|---|---|---|---|
| | 2 hours (sc) | 24 hours (po) | 1–6 hours (sc) |
| 1 | 0.099 | 0.085 | 39 |
| 3 | | | 17 |
| 4 | 0.070 | <0.0056 | >45 |
| 5 | 0.055 | 0.0097 | >45 |
| 6 | 0.020 | 0.012 | 30 |
| 7a | | | >42 |
| 7b | | | >21 |
| 8 | 0.035 | 0.013 | >43 |
| 9 | 0.13 | 0.078 | >43 |
| 10 | 0.33 | | >30 |
| 12 | 0.076 | 0.037 | >40 |
| 13 | 0.088 | 0.45 | >40 |
| sertindole | 0.035 | 0.039 | >91 |

Some of the compounds of the invention have also been found to inhibit the firing of spontaneously active DA neurones in the ventral tegmental area of the brain upon 21 days of repeated oral treatment of rats. The test wich was performed according to the method described by Skarsfeldt, T. and Perregaard, J., Eur. J. Pharmacol. 1990, 182, 613–614 is indicative of antipsychotic effects in humans.

Results

It appears from Table 1 that, like sertindole, the compounds of the invention have affinity for the serotonin 5-HT$_2$ receptor and the dopamine D$_2$ receptor, respectively. Furthermore, it is seen from the in vivo test data in Table 2

Formulation Examples

The pharmaceutical formulations of the invention may be prepared by conventional methods in the art.

For example: Tablets may be prepared by mixing the active ingredient with ordinary adjuvants and/or diluents and subsequently compressing the mixture in a conventional tabletting machine. Examples of adjuvants or diluents comprise: corn starch, lactose, talcum, magnesium stearate, gelatine, lactose, gums, and the like. Any other adjuvant or additive colourings, aroma, preservatives etc. may be used provided that they are compatible with the active ingredients.

Solutions for injections may be prepared by solving the active ingredient and possible additives in a part of the vehicle, preferably sterile water, adjusting the solution to the desired volume, sterilization of the solution and filling in suitable ampules or vials. Any suitable additive conventionally used in the art may be added, such as tonicity agents, preservatives, antioxidants, etc.

Typical examples of recipes for the formulations of the invention are as follows:

| 1) Tablets containing 5 milligrams of Compound 6 calculated as the free base: | |
|---|---|
| Compound 6 | 5.0 mg |
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |

| 2) Tablets containing 1 milligram of Compound 8 calculated as the free base: | |
|---|---|
| Compound 8 | 1.0 mg |
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |

| 3) Syrup containing per milliliter: | |
|---|---|
| Compound 4 | 5.0 mg |
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 ml |
| Flavour | 0.05 mg |
| Saccharin natrium | 0.5 mg |
| Water | ad 1 ml |

| 4) Solution for injection containing per milliliter: | |
|---|---|
| Compound 6 | 0.5 mg |
| Sorbitol | 5.1 mg |
| Acetic acid | 0.08 mg |
| Water for injection | ad 1 ml | that the compounds are substantally non-cataleptogenic, potent and long-lasting 5-$HT_2$ antagonists in vivo.

We claim:

1. A phenylindole compound having formula

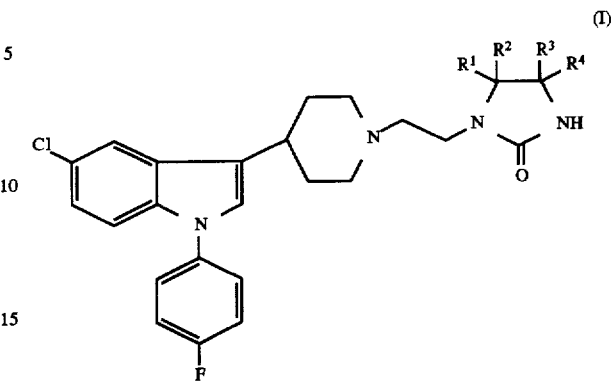

(I)

wherein $R^1$-$R^4$ are independently selected from the group consisting of hydrogen, deuterium, halogen, $C_{1-6}$ alkyl, cycloalkyl, cycloalkyl-$C_{1-6}$ alkyl, aryl-$C_{1-6}$ alkyl, aryl, hydroxy, $C_{1-6}$ alkoxy, cycloalkyloxy, cycloalkyl-$C_{1-6}$ alkyloxy, aryl-$C_{1-6}$ alkyloxy, aryloxy, $C_{1-6}$ alkylthio, cycloalkylthio, cycloalkyl-$C_{1-6}$ alkylthio, aryl-$C_{1-6}$ alkylthio and arylthio, with the proviso that all 4 substituents cannot be hydrogen; or at least one pair of substituents ($R^1$, $R^2$ or $R^3$, $R^4$) constitutes an oxo group or a thioxo group and, if only one oxo or thioxo group is present, the other two substituents are selected from the above group defined for $R^1$-$R^4$, with the proviso that they may not both be hydrogen; or $R^1$ and $R^2$ and/or $R^3$ and $R^4$, respectively, can be joined together to form a 3–8 membered spiro ring optionally containing one oxygen or sulfur atom in the ring; or acid addition salt thereof.

2. A compound according to claim 1, wherein $R^1$-$R^4$ are individually selected from the group consisting of hydrogen, deuterium, lower alkyl, hydroxy and lower alkoxy; or one or both pair of substituents ($R^1$ and $R^2$ or $R^3$ and $R^4$) constitute an oxo group or are joined together to form a 3–8 membered spiro ring.

3. A compound according to claim 1, wherein both substituents of at least one pair of substituents ($R^1$ and $R^2$ or $R^3$ and $R^4$) are both different from hydrogen or constitute together an oxo group or are joined to form a spiro ring.

4. A pharmaceutical composition, wherein said composition comprises a compound according to claim 1 together with a pharmaceutically acceptable carrier or diluent.

5. A compound according to claim 3, wherein at least one of ($R^1$ and $R^2$ or $R^3$ and $R^4$) taken together is oxo.

6. A method for treatment of psychosis, depression, negative symptoms of schizophrenia, hypertension or extrapyramidal side effects induced by antipsychotic drugs comprising administration, to a patient in need of said treatment, a pharmaceutical composition according to claim 4.

* * * * *